United States Patent
Tzachar et al.

(10) Patent No.: US 11,006,933 B2
(45) Date of Patent: May 18, 2021

(54) DEVICE AND METHOD FOR INSERTING A CANNULA TO A PREDETERMINED DEPTH WITHIN A BONE, IRRESPECTIVE OF THE THICKNESS OF THE TISSUE ABOVE THE BONE

(71) Applicant: WAISMED LTD., Herzliya (IL)

(72) Inventors: Barak Tzachar, Petach Tikva (IL); Alexander Kalnitskiy, Maale Adumim (IL); Yosef Gomberg, Psagot (IL)

(73) Assignee: WAISMED LTD., Herzliya (IL)

( * ) Notice: Subject to any disclaimer, the term of this patent is extended or adjusted under 35 U.S.C. 154(b) by 63 days.

(21) Appl. No.: 16/190,568

(22) Filed: Nov. 14, 2018

(65) Prior Publication Data

US 2019/0076132 A1 Mar. 14, 2019

Related U.S. Application Data

(63) Continuation of application No. 15/384,676, filed on Dec. 20, 2016, now Pat. No. 10,136,878.

(30) Foreign Application Priority Data

Dec. 24, 2015 (IL) .......................................... 243347

(51) Int. Cl.
*A61B 10/02* (2006.01)
*A61M 5/32* (2006.01)
(Continued)

(52) U.S. Cl.
CPC ......... *A61B 10/025* (2013.01); *A61M 5/3287* (2013.01); *A61M 5/46* (2013.01);
(Continued)

(58) Field of Classification Search
CPC ........... A61B 17/3472; A61B 17/3403; A61M 2005/1585; A61M 2210/02; A61M 5/46; A61M 5/427
See application file for complete search history.

(56) References Cited

U.S. PATENT DOCUMENTS 3,815,605 A * 6/1974 Schmidt ............ A61M 39/0247
606/182
5,817,052 A 10/1998 Johnson et al.
(Continued)

OTHER PUBLICATIONS

Israeli Patent and Trademark Office's ("ILPTO") website for Israeli patent application serial No. 221183; (1 page) Erroneously available on Nov. 11, 2014.
(Continued)

*Primary Examiner* — Emily L Schmidt
(74) *Attorney, Agent, or Firm* — Roach, Brown, McCarthy & Gruber, P.C.; Kevin D. McCarthy

(57) ABSTRACT

An intraosseous device, comprising a cannula through which life-saving fluids are transfusible into or out of bone marrow of a target bone when the cannula is penetrated into the target bone; a stylet which is engageable with the cannula; and means for causing penetration of the stylet and cannula, when mutually engaged, to a predefined depth α within the target bone with respect to an outer surface of the target bone, the depth α being irrespective of a thickness of tissue above the target bone.

13 Claims, 17 Drawing Sheets

(51) Int. Cl.
*A61M 5/46* (2006.01)
*A61B 90/00* (2016.01)

(52) U.S. Cl.
CPC ............... *A61B 2010/0208* (2013.01); *A61B 2010/0258* (2013.01); *A61B 2090/036* (2016.02); *A61M 2202/10* (2013.01); *A61M 2205/0216* (2013.01); *A61M 2210/02* (2013.01)

(56) References Cited

U.S. PATENT DOCUMENTS

| | | | |
|---|---|---|---|
| D633,199 S | 2/2011 | MacKay et al. | |
| 2003/0225344 A1 | 12/2003 | Miller | |
| 2003/0225411 A1 | 12/2003 | Miller | |
| 2004/0220497 A1* | 11/2004 | Findlay | A61M 5/32 600/562 |
| 2005/0131345 A1* | 6/2005 | Miller | A61B 17/3476 604/117 |
| 2005/0171504 A1 | 8/2005 | Miller | |
| 2006/0015066 A1 | 1/2006 | Turieo et al. | |
| 2006/0052790 A1 | 3/2006 | Miller | |
| 2008/0208136 A1 | 8/2008 | Findlay et al. | |
| 2010/0137740 A1 | 6/2010 | Miller | |
| 2010/0152616 A1* | 6/2010 | Beyhan | A61B 10/025 600/568 |
| 2010/0160867 A1 | 6/2010 | Miller et al. | |
| 2010/0160868 A1 | 6/2010 | Miller et al. | |
| 2010/0298830 A1 | 11/2010 | Browne et al. | |
| 2010/0298831 A1 | 11/2010 | Browne et al. | |
| 2010/0312246 A1 | 12/2010 | Browne et al. | |

OTHER PUBLICATIONS

Same as Non-Patent Literature document 1 except it identifies by Appendix Nos. 2 to 8 where a person skilled in the art could obtain and download Non-Patent Literature documents 3 to 8; prepared prior to Jan. 30, 2017.

ILPTO's Notice to the Applicant's Israeli attorneys received on Jan. 5, 2014, notifying that the application will be published on Jan. 30, 2014, unless the Applicant notifies the ILPTO that the Applicant wishes to abandon the application, and in that case, the application will Not be published (1 page); Erroneously available on Nov. 11, 2014.

Email that Applicant's Israeli attorneys sent to the ILPTO on Jan. 9, 2014, demanding the abandonment of Israeli patent application serial No. 221183 (1 page); Erroneously available on Nov. 11, 2014.

The Jan. 9, 2014 letter that Applicant's Israeli attorneys attached to the Jan. 9, 2017 email identified as Non-Patent Literature document 4 (1 page); Erroneously available on Nov. 11, 2014.

The ILPTO letter dated Jan. 9, 2014 clearly indicating that Israeli patent application serial No. 221183 has been canceled following the Applicant's request dated Jan. 9, 2014 (1 page); Erroneously available on Nov. 11, 2014.

The specification, claims and drawings respectively, of Israeli patent application serial No. 221183 as uploaded to the ILPTO website on Nov. 11, 2014 and erroneously published on Nov. 11, 2014 (38 pages); Erroneously available on Nov. 11, 2014.

The application form of Israeli patent application serial No. 221183 (1 page); Erroneously available on Nov. 11, 2014.

\* cited by examiner

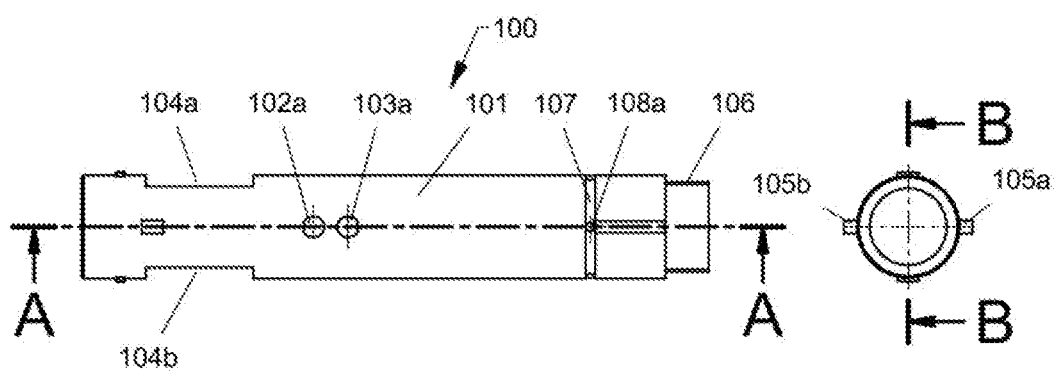
FIG. 4a
FIG. 4b
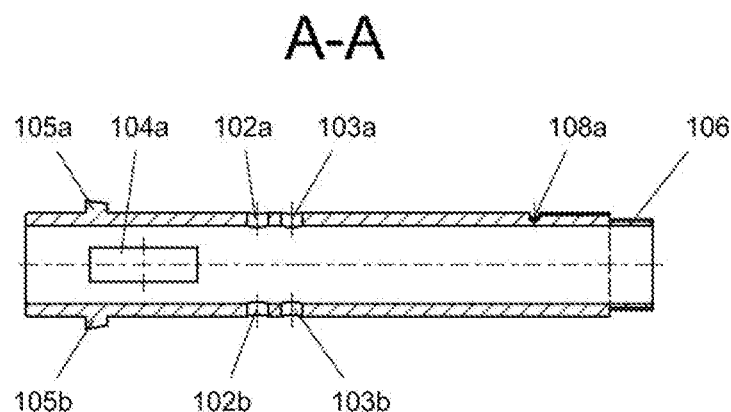
FIG. 4c

B-B

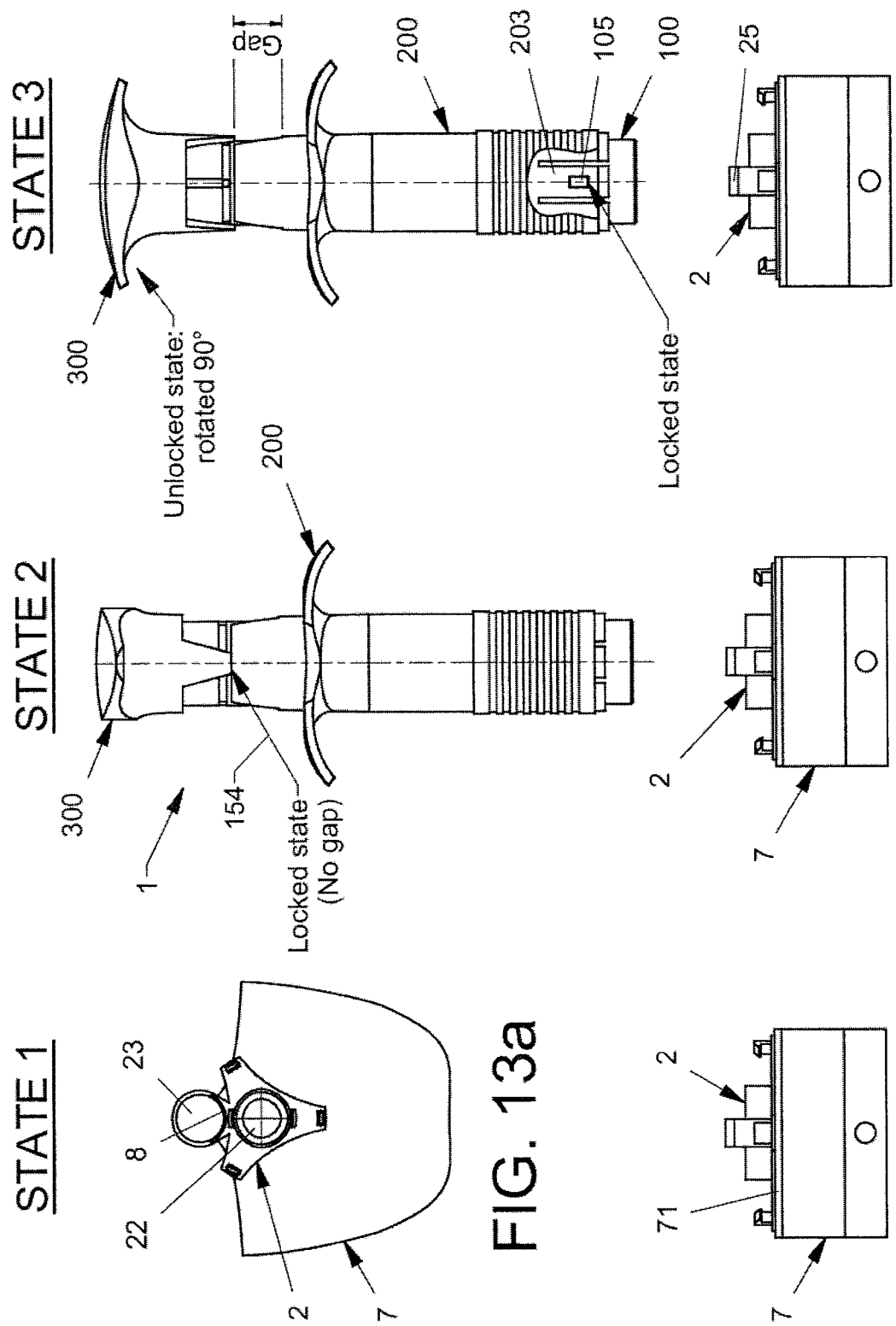

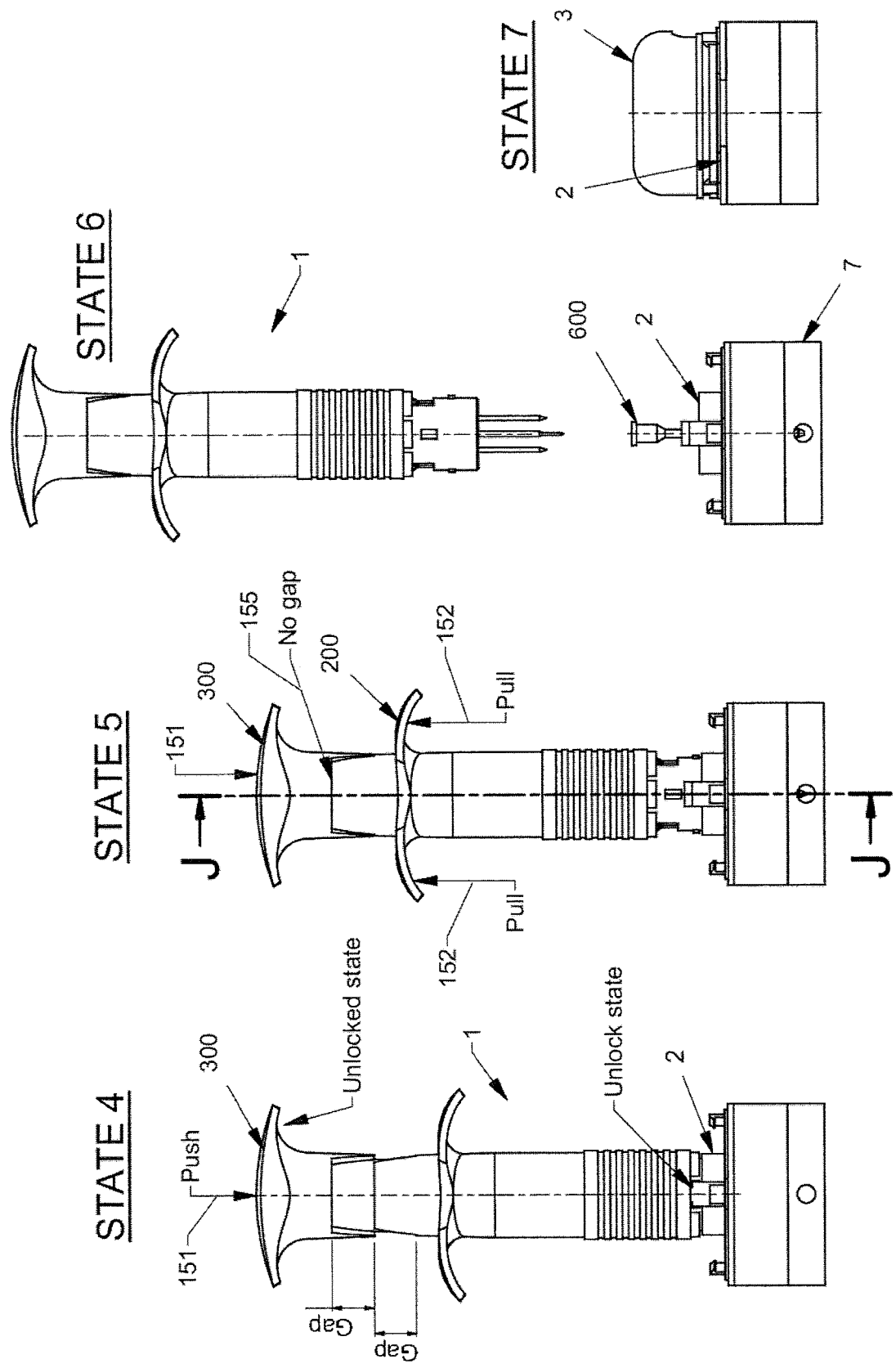

DEVICE AND METHOD FOR INSERTING A CANNULA TO A PREDETERMINED DEPTH WITHIN A BONE, IRRESPECTIVE OF THE THICKNESS OF THE TISSUE ABOVE THE BONE

This application is a continuation of U.S. application Ser. No. 15/384,676 filed on Dec. 20, 2016.

FIELD OF THE INVENTION

The present invention relates to instruments for the insertion of a cannula into a bone of a patient, particularly the sternum, for the purpose of administration of drugs fluids and blood or for the aspiration of samples of a bone marrow through said cannula. More specifically, the invention relates to such a device which comprises automatic means for causing the insertion of the cannula into a predefined depth within the bone, no matter what is the depth of the tissue above the bone, particularly the sternum. The device is also comprises more safety means than prior art devices. The invention also relates to a kit for enabling a safer and more reliable and accurate operation of the device of the invention.

BACKGROUND OF THE INVENTION

Intraosseous devices for causing at least a portion of a needle assembly (which comprises a cannula) to penetrate into a bone are well known in the art. Such devices are typically used in life saving cases where the injection of drugs to the blood circuitry is required, while it is difficult for the medical staff to locate the patient's vein within a reasonable time. This device is also used for the extraction of a sample from a patient's bone marrow.

There are several specific locations at the patient's body where this procedure can be performed, such as the proximal Tibia, Distal Tibia, Humeral Head, and Distal Radius. One preferred location at the patient's body where this procedure is typically performed is the sternum, which is located at the upper chest. More specifically, the insertion is typically performed on the Manubrium, which is the upper part on the Sternum.

However, there are several problems that are associated with an intraosseous procedure which is performed at the sternum (but may exist also at other bone locations), or that are associated with prior art devices, as follows:

a. The sternum has a relatively small surface, while it is very important to perform the procedure exactly at the sternum center. Therefore, additional means have to be provided in order to exactly determine the penetration location prior to performance of the procedure;

b. The sternum is fragile, and may break if the penetration is not performed exactly at the sternum center, or if it is performed with an excessive force. If the procedure results in breakage of the sternum, the procedure fails causing an additional damage to the patient and a serious threat for his life;

c. From the above described problems it becomes clear that an intraosseous device has to introduce the cannula very accurately at the sternum center. Moreover, the penetration depth to the sternum (i.e., beyond the sternum front surface) has to be made very accurately (typically to a depth of 6 mm) in order for the procedure to succeed. However, unfortunately it has been found that typical automatic intraosseous devices at which the penetration depth is predefined cannot efficiently operate at the sternum. This is particularly due to the fact that in those prior art devices the user typically adjusts the total penetration depth, which is a sum of the thickness of the tissue above the bone and the of the penetration depth of the cannula to the bone (herein, the term "tissue above the bone" refers to the tissue which is located between the bone, such as the sternum, and the patient's skin). However, such a total penetration depth definition cannot reliably operate at the sternum, as it is known in the art that the thickness of tissue above the sternum very significantly vary from one person to another, leaving the actual penetration depth to sternum to be very inaccurate. Although several of prior art devices overcome this problem, still these devices suffer from other problems, i.e., of being non-automatic devices, from being unsafe or inaccurate with respect to the penetration location, etc.;

d. Still another problem relates to the safety of operation issue. Typically, prior art devices are provided some safety means (such as a safety catch) for preventing erroneous operation. However, none of said safety means is connected to the appropriate location of the penetration, once this location has been determined. More specifically, other prior art devices may be operated on other locations of the human body once their safety means have been released. It is desired to provide a device which becomes operable (by the release of one of its safety means) only at the correct location, once this location has been determined;

e. Several prior art device for the injection to the sternum still suffer from the drawback they are not automatic, requiring the user to perform a relatively complicated manipulation. It is desired to provide a fully automatic device, which still resolves all the above problems.

U.S. D 633,199, U.S. Pat. No. 5,817,052, US 2010/0298830, US 2010/0160868, US 2003/0225344, US 2010/0298831, US 2008/0208136, US 2006/0015066, US 2010/0160867, US 2010/0152616, US 2010/0137740, US 2006/0052790, US 2005/0171504, US 2003/0225411, and US 2010/0312246, all describe some sorts of intraosseous devices, at least some of them describe means for the introduction of as cannula into the sternum.

FASTx™ Literature Review and Bibliography (publication date is unknown), http://www.pyng.com, provides some background and a structure of device for the introduction of a cannula into the sternum.

It is therefore an object of the present invention to provide an automatic intraosseous device that can introduce a cannula to a specific depth of a bone, irrespective of the thickness of the tissue above the bone.

It is another embodiment of the invention to provide a kit which comprises, in additional to the automatic intraosseous device, means for accurately determining the right location for penetration, particularly when this location is the sternum.

It is still another object of the present invention to provide safety means at said device that releases the device from a locked position, only when the device is positioned at the right location for penetration, once this location has been determined, while preventing any operation at other locations.

It is still an object of the present invention to provide all said features and advantages in a device which is fully automatic.

Other objects and advantages of the invention will become apparent as the description proceeds.

SUMMARY OF THE INVENTION

The invention relates to an automatic device for the insertion of a stylet and cannula to a predefined depth $\alpha$ within a bone, said depth $\alpha$ being irrespective of the thickness of the tissue above the bone, which comprises: (a) a trigger unit for activating the device; (b) a barrel; (c) a probe unit within said barrel which is driven by a secondary spring, said probe unit comprises one or more probing needles at a distal end, and an anvil at a proximal end for defining an end of movement location for a hammer unit; (d) a hammer unit which is driven by a main spring, said hammer unit comprises a stylet at its distal end, a core at its proximal end, and a piston in between said core and stylet, wherein said stylet is inserted to within a cannula, and wherein when said hammer unit is positioned at said end of movement location, a tip of the stylet which is longer than said one or more probing needles is located a distance $\alpha$ farther to the distal direction from the respective ends of said probing needles; and (e) one or more grasping units; wherein activation of said trigger unit follows by, (f) release of said second spring which in turn pushes said probing needles of said probe unit toward the patient's bone, up to a point of contact with the bone surface; (g) grasp of the anvil of said probe unit by said grasping units, when said contact of the probing needles with the patient's bone occurs; and (h) release of said main spring, which in turn pushes said hammer unit up to said end of movement location, thereby inserting said cannula to a depth of $\alpha$ within the patient's bone.

Preferably, the device further comprises a first safety means having safety catch configuration, and second safety means.

The invention also relates to a kit which comprises the device as described above, and further comprising a positioning element, which in turn comprises: (a) means for determining the right point on the patient's body for the stylet and cannula insertion; and (b) means for releasing said second safety means of the device only when the device is appropriately positioned on said positioning element, thereby enabling activation of the device only at said determined right point of insertion.

Preferably said means at the positioning element for the release of said second safety means of the device are one or more peripheral snaps, that open corresponding beveled snaps at said device, thereby enabling operation of the device.

Preferably, the removal of the device from said positioning element after the release of said second safety means, however without activation of the device, returns the second safety means of the device into a locked state.

Preferably, said kit also comprises a cover for covering the positioning element at the after the device operation.

BRIEF DESCRIPTION OF THE DRAWINGS

In the drawings:

FIGS. 13a-13h illustrate various steps by which the device of the invention operates.

DETAILED DESCRIPTION OF PREFERRED EMBODIMENTS

Figure 1:
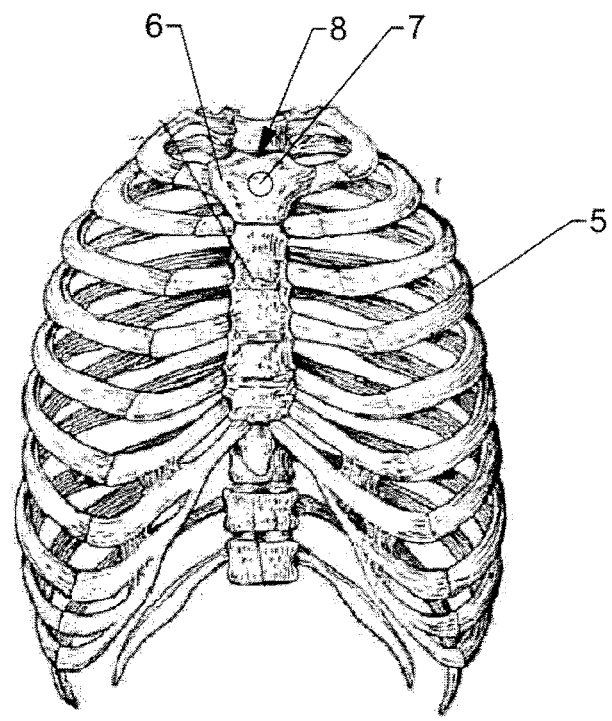
FIG. 1 generally shows the structure of a person's chest.

The present invention relates to a sternum injection device (hereinafter, SID, or briefly "the device"). The SID of the invention enables introduction of fluid into a bone, particularly the sternum. As will be elaborated hereinafter, the device of the present invention provides a cannula into a predefined depth of a bone, irrespective of the thickness of the tissue above the bone. The device is particularly adapted to the insertion of a cannula into the sternum, and the following discussion assumes that the target bone is the sternum. However, the injection into the sternum should not limit the invention, as the device may be used with respect to other bone locations as well. Thereafter, after the introduction of the cannula into the bone, the fluid can be provided through the cannula to within the sternum. The SID of the invention is typically used in emergency cases, where injection into the sternum provides the fastest and most efficient effect. Moreover, the device can be used in cases when there is a need to obtain a sample from the bone marrow, for diagnosis purposes.

The SID of the present invention is essentially a spring loaded device. Upon its activation, the device "shoots" a stylet and cannula by a force generated by the spring expansion, causing the stylet and cannula that are a part of a needle assembly, to penetrate into the bone. The device of the invention is provided with means for automatically adjusting the depth of the insertion to the thickness of the tissue above the sternum. This is an important feature of the invention, as it has been found that the tissue thickness significantly varies between various people. It has been found by the inventors that without having such an adjustment feature, the cannula introduction fails in a significant portion of the total cases.

The automatic adjusting means comprises first driving means and second driving means. The first driving means comprises a first force transmitting unit that transmits a force to a pointed object which causes the latter to be driven through tissue above the target bone to a point of contact with a surface of the target bone. The second driving means is responsive to a triggered action and comprises a second force transmitting unit that transmits a force to the stylet, such as with use of a plurality of cooperating mechanical elements, which transmitted force causes the stylet to be driven until the distal tip of the stylet is penetrated within the target bone and spaced distally from the distal tip of the pointed object by a predefined depth.

To define the predetermined depth, first and second reference elements of the first and second driving means, respectively, interface with the respective driving means such that they are configured to be separated by a predetermined distance both when set in a retracted position and subsequently in a driven position after having been separated by a distance greater than the predetermined distance following distal displacement of the pointed object. A force absorbing unit of the first driving means limits movement of a stylet-driving member of the second driving means to ensure a separation between the first and second reference elements that is equal to the predetermined distance.

As will also be shown in detail, the device further comprises two safety measures for preventing erroneous or accidental operation. The first safety measure of the SID requires the user to make a turn of a safety catch (such as a 90° turn), and the second safety measure requires the user to apply a linear force directed against a positioning element which is attached to the patient's body. Only after conforming to the requirements of said two safety measures, the device is operable. In such a manner, the device becomes more reliable with respect to the determination of the penetration location and with respect to depth of the cannula insertion, and erroneous or accidental operations are prevented.

FIG. 1 generally shows the structure of a person's chest 5. The Manubrium 6 is relatively small in size, and the site of penetration 7 has to be made very accurately, at a specific distance, typically about 15 mm from the sternal notch 8.

Figure 2:
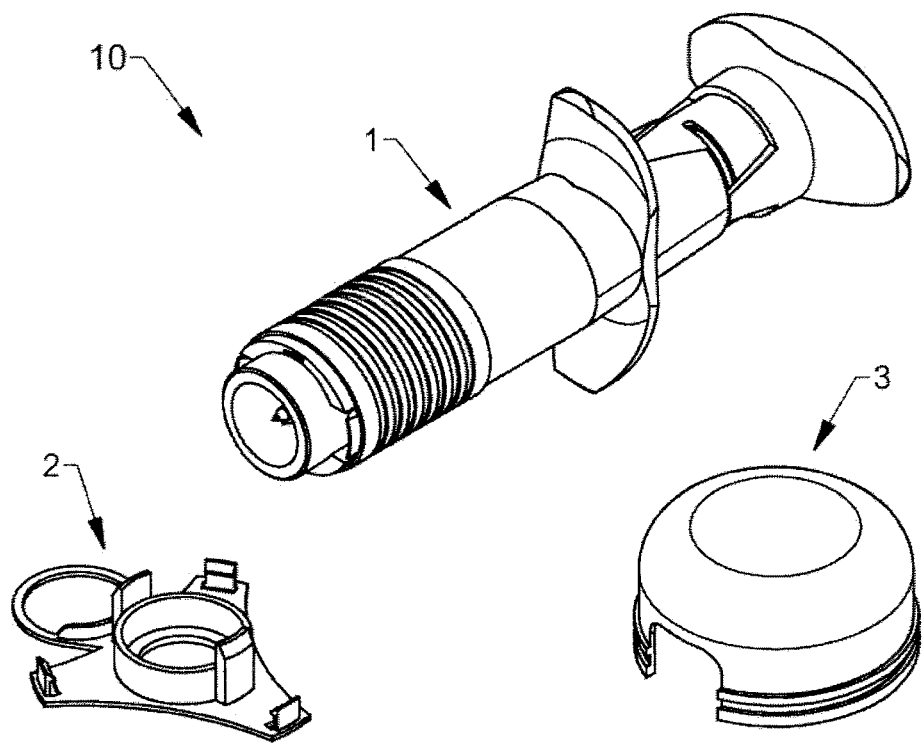
FIG. 2 shows a kit according to an embodiment of the present invention.

The kit 10 of the invention is shown in FIG. 2. The kit comprises the device 1, a positioning element 2, and cover 3.

Figure 3:
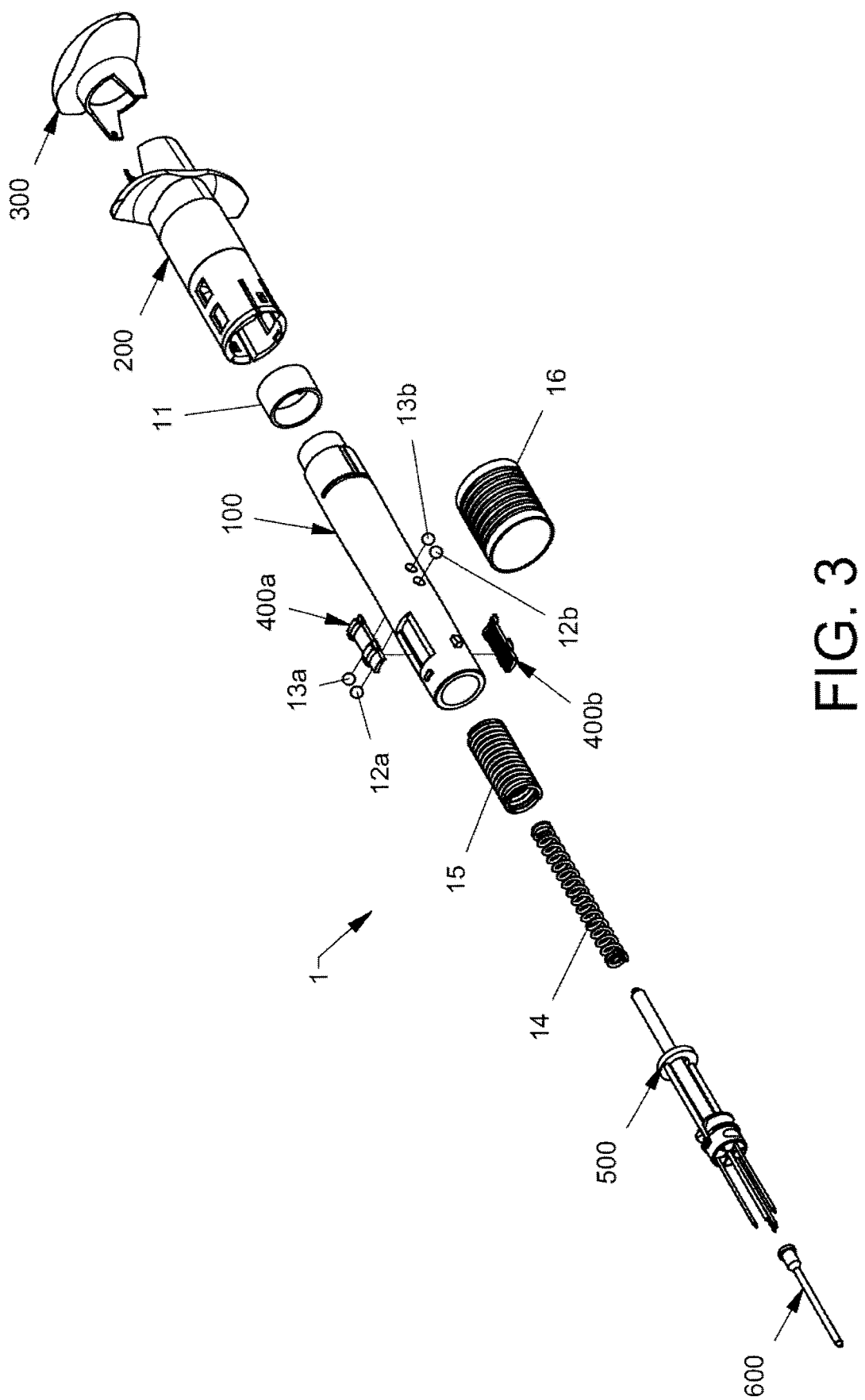
FIG. 3 is an exploded view of the device of the invention.

An exploded view of the device 1 is shown in FIG. 3. The device comprises barrel 100, rear cap 11, trigger 200, safety catch 300, two grasping elements 400a and 400b, two pairs of balls 12a, 12b, 13a and 13b, main spring 14, secondary spring 15, needles assembly 500, cannula 600 and a decorative jacket 16.

For the sake of convenience, the safety catch 300 defines a proximal end (or direction) of the device 1, and similarly, the cannula 600 defines a distal end (or direction) of the device 1.

Figure 4D:
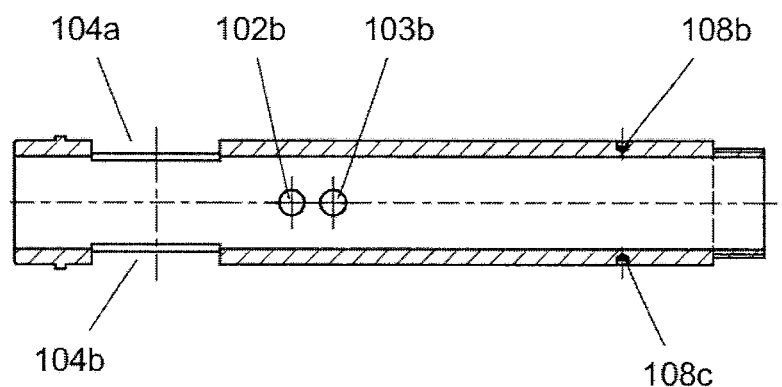
FIGS. 4a-4c show various views of the barrel of the device.
Figure 4E:
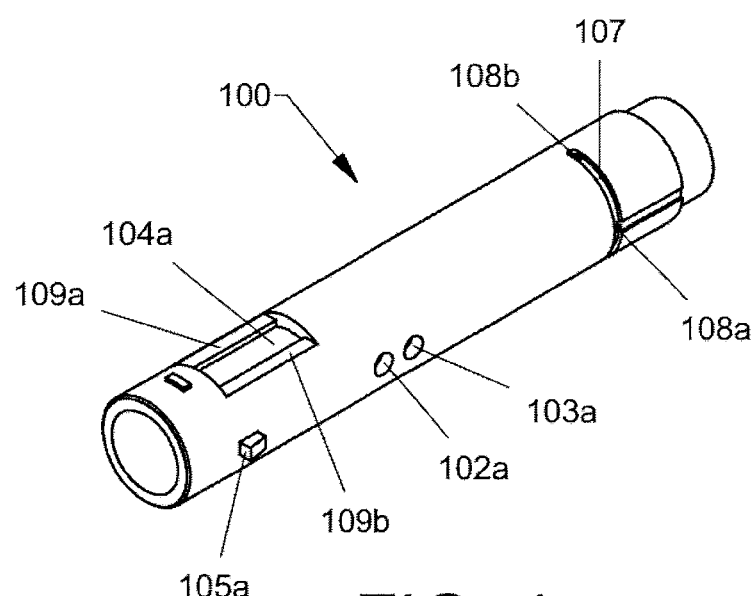

FIG. 4a shows a side view of barrel 100, FIG. 4b shows a front view of the barrel, FIG. 4c shows a cross sectional view of the barrel made along plane A-A of FIG. 4a, FIG. 4d shows a cross sectional view of the barrel 100 along plane B-B of FIG. 4b, and FIG. 4e is an isometric view of barrel 100. The barrel 100 is used for containing the needles assembly 500 in a cocked configuration prior to the device activation, and for directing the needles assembly toward the patient's body. The barrel is essentially a tube 101, having two pairs of holes 102a, 102b, 103a and 103b, for the insertion thereof of said balls 12a, 12b, 13a and 13b respectively (see FIG. 3). The barrel further comprises two windows 104a and 104b, for placement of the two grasping elements 400a and 400b, respectively. More specifically, each of said two windows comprises two side shelves 109a, and 109b shown in FIG. 4e for preventing the grasping elements from falling to within the internal space of the barrel 100. The barrel further comprises on its external surface, close to its distal end, a pair of protrusions 105a and 105b for joining with snaps 203a and 203b of trigger 200 (see FIGS. 5a to 5f). At the proximal end of the barrel 100, there is a thread 106 by which the rear cap 11 is joined with barrel 100. The barrel 100 further comprises on its external surface a groove 107, which comprises three indexing recesses 108a, 108b, and 108c, for fixing the safety catch 300 in one of the states: a locked state (when positioned in recess 108a), or one of two unlocked states (when positioned in recesses 108b or 108c respectively).

Figure 5A:
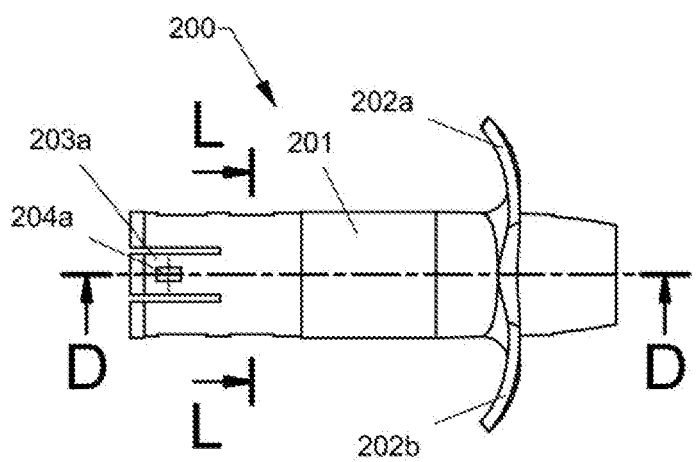
FIGS. 5a-5f show various views of the trigger of the device.
Figure 5B:
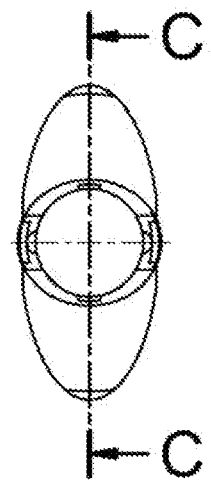
Figure 5C:
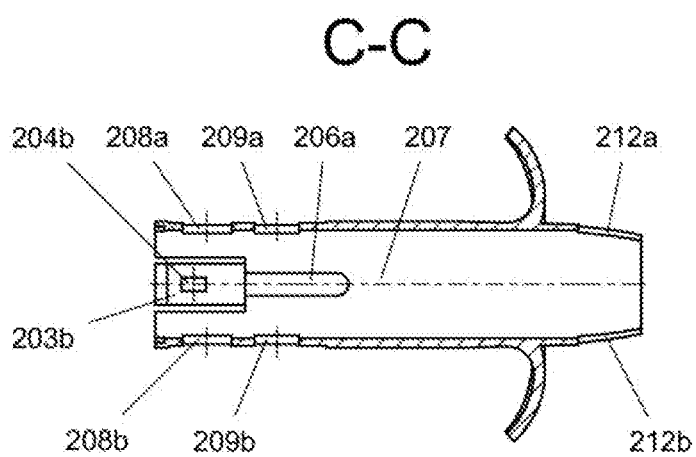
Figure 5D:
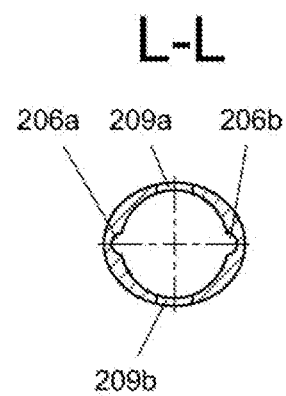
Figure 5E:
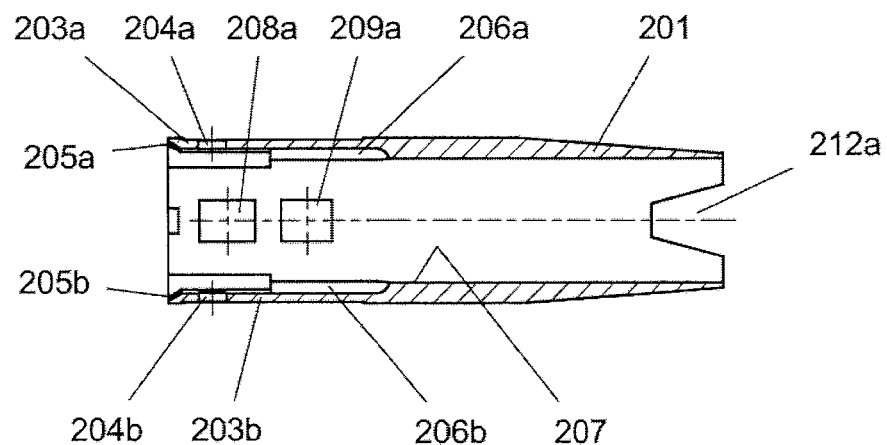
Figure 5F:
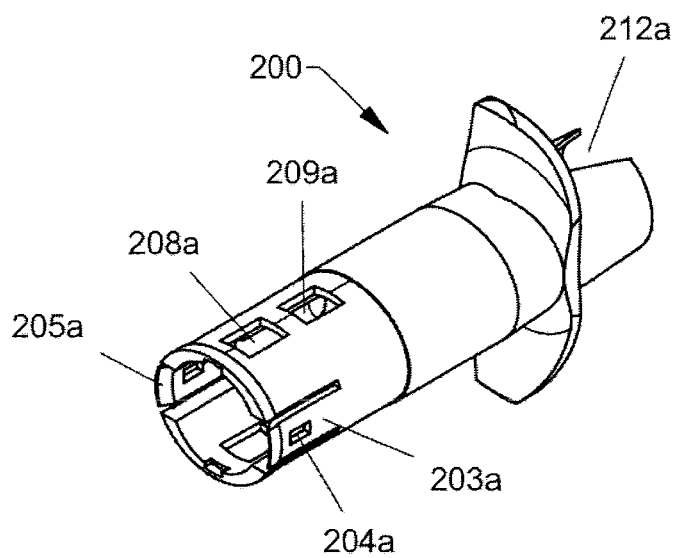

FIG. 5a shows a side view of trigger 200, FIG. 5b shows a front view of the trigger, FIG. 5c shows a cross sectional view of trigger 200, made along plane C-C of FIG. 5b, FIG. 5d shows a cross sectional view of trigger 200, made at plane L-L of FIG. 5a, FIG. 5e shows a cross sectional view of trigger 200, made along plane D-D of FIG. 5a, and FIG. 5f is an isometric view of trigger 200.

Trigger 200 is used for activating the device 1. The trigger 200 comprises tubular casing 201 having two release wings 202a and 202b that are positioned at the proximal end. At the distal end of trigger 200, there is a pair of snaps 203a and 203b that are used for coupling with barrel 100. More specifically, each of the snaps 203a and 203b has a window 204a and 204b respectively, for accommodating one of the protrusions 105a and 105b of the barrel 100, respectively. Each of the snaps 203a and 203b is provided with a bevel 205a and 205b respectively. When the device is appropriately placed on placement element 2 (see FIGS. 10a-10c), the pair of protruding fingers 25a and 25b open the snaps 203a and 203b, enabling the trigger 200 to disconnect from barrel 100, thereby enabling activation of the device 1. Therefore, the beveled snaps 203a and 203b, together with protrusions 105a and 105b and fingers 25a and 25b form a second safety mechanism of the device, in addition to safety catch 300 (which forms a first safety mechanism). More specifically, only if the following two safety measures are met, the device 1 can be activated: (i) the safety catch 300 has been previously unlocked, and (ii) the device has been appropriately placed on the placement element 2.

Figure 8A:
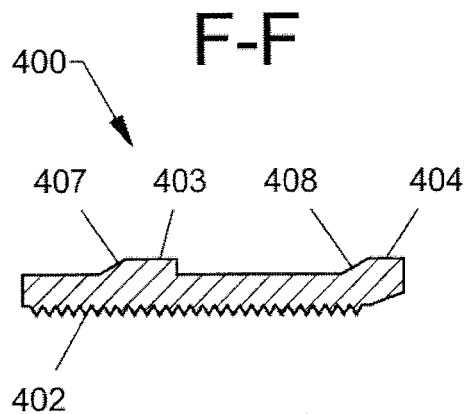
FIGS. 8a-8d show various views of the grasping elements of the device.
Figure 8B:
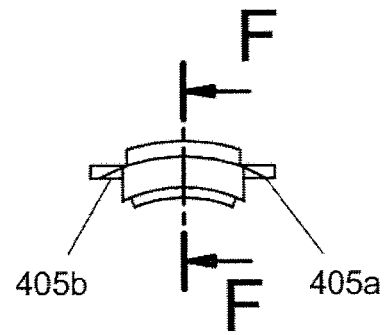
Figure 8C:
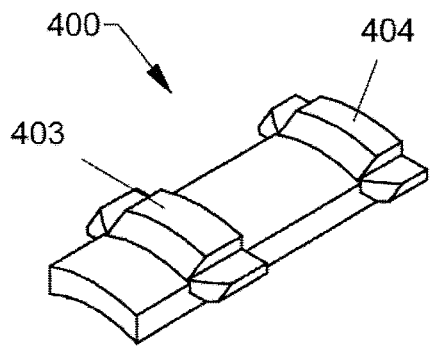
Figure 8D:
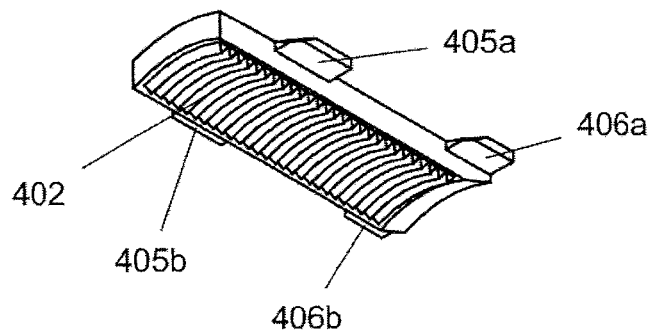

The internal surface 207 of trigger 200 comprises two longitudinal grooves 206a and 206b. Originally, balls 12a, 12b, 13a, and 13b are out of the grooves 206a and 206b, engaging the main portion of internal surface 207, therefore causing the device to be cocked. Trigger 200 further comprises two pairs of windows 208a, 208b, 209a, and 209b for accommodating the extensions 403 and 404 of the grasping elements 400, as shown in FIGS. 8a-8c. The trigger 200 further comprises at its proximal end two openings 212a and 212b. The openings 212a and 212b enable pulling and movement of the trigger 200 to the proximal direction relative to barrel 100, when safety catch 300 is unlocked. On the other hand, such pulling and movement are prevented during the locked state of the safety catch 300.

Figure 6A:
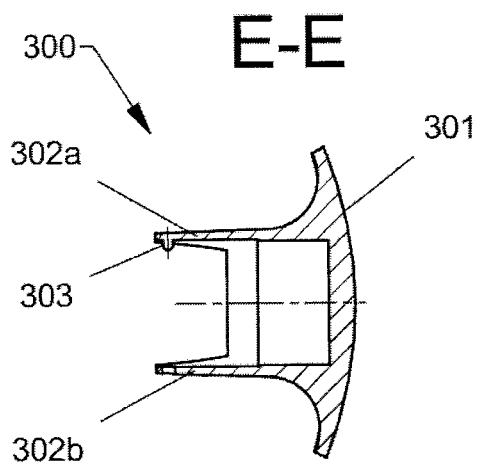
FIGS. 6a-6c show various views of the safety catch of the device.
Figure 6C:
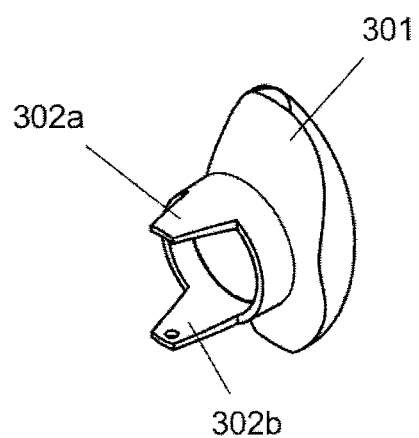
Figure 6B:
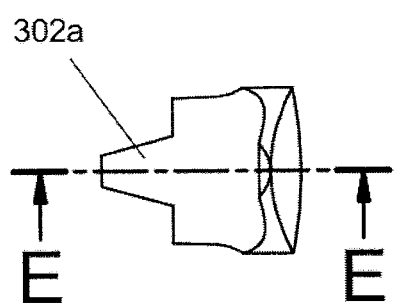

As previously noted, safety catch 300 is one of the two safety means of the device 1. FIG. 6a shows a cross section of safety catch 300 made along plane E-E of FIG. 6b. FIG. 6b shows a top view of safety catch 300, and FIG. 6c is an isometric view of safety catch 300. The safety catch 300 is essentially a knob 301 having two tongues 302a and 302b. The internal surface of one of said tongues 302 comprises an indexing protrusion 303. Said indexing protrusion engages one of the indexing recesses 108a (defining a locked state of the device), 108b, or 108c (both recesses 108b or 108c define an unlocked state), respectively. It should be noted that the device may include only one locked state, and one unlocked state (instead of said two positions for unlocked state as described). The two unlocked positions are provided for the sake of convenience of right-hand and left-hand users.

Figure 7A:
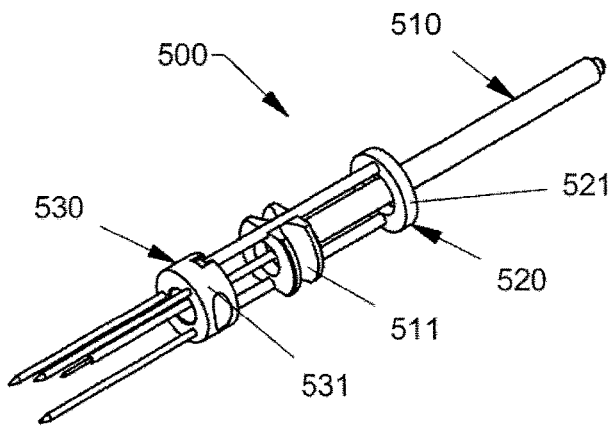
FIGS. 7a and 7b show various views of the needles assembly.
Figure 7B:
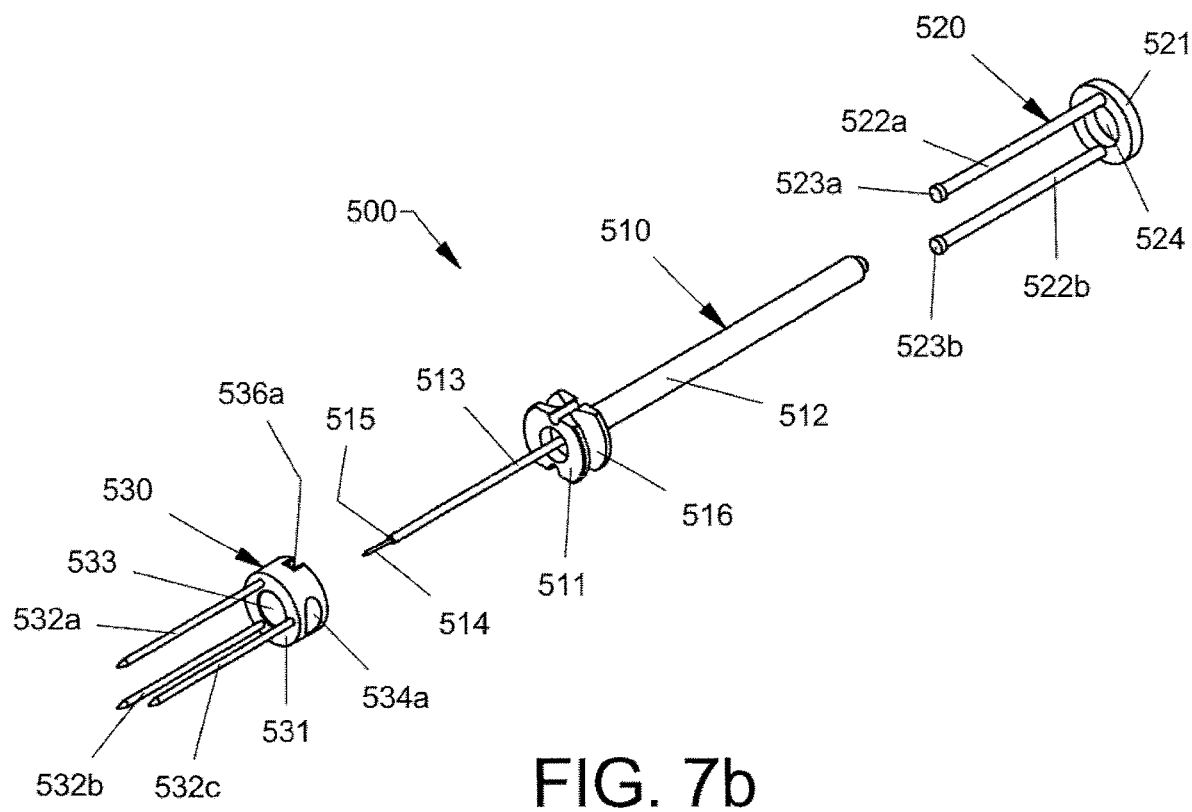

The needle assembly 500 (shown in FIGS. 7a and 7b) is used for penetrating the cannula 600 into the bone. After the activation of the device, the needle assembly is forcibly sent towards the bone. At a first stage, the thickness of the tissue above the sternum is measured by the first driving means, and at a second stage the stylet and cannula are caused to be penetrated by the second driving means to a predefined depth within the sternum, which is irrespective of the thickness of the tissue above the bone. More specifically, the device uses the measured tissue thickness in order to enable penetration to exactly the predefined depth within the bone. FIG. 7a is an isometric view of the needle assembly, and FIG. 7b is an exploded isometric view of the needle assembly. The needle assembly 500 comprises hammer unit 510, driver unit 520, and probe unit 530. Hammer unit of the second driving means comprises the cooperating mechanical elements of piston 511, core 512, and stylet 513. Piston 511 comprises groove 516 for accommodating balls 13a and 13b. The end 514 of stylet 513 is of smaller diameter than the rest of the body of the stylet. The end of stylet 514 has a peripheral face 515 for engaging with a corresponding face 604 of cannula 600 (see FIG. 9), thereby pushing the cannula 600 to the bone. The driver unit 520 of the first driving means comprises a ring 521, and two rods 522a and 522b. Each of the rods comprises a base 523a and 523b respectively, for joining with anvil 531 of probe unit 530. More specifically, the bases 523a and 523b are latched or fixed to the anvil 531 in any appropriate manner. Probe unit 530 comprises anvil 531, and three probing needles 532. The anvil, at its center, comprises a round opening 533, through which the stylet 513 enters. The external surface of anvil 531 comprises two opposing recesses 534a and 534b for balls 12a and 12b respectively. The rest of the external surface of anvil 531 is rough, for enabling the grasping elements 400a and 400b to hold the anvil 531 at the appropriate time, as will be elaborated later. The anvil 531 further comprises two corresponding latches 536a and 536b, of other fixing means for maintaining the bases 523a and 523b connected to the anvil.

FIG. 7a shows the needle assembly in its combined form. More specifically, core 512 of hammer 510 is inserted into round opening 524 of ring 521, while the rods 522a and 522b are maintained fixed to anvil 531 by means of bases 523a and 523b and the corresponding latches of the anvil. In the combined state of the needle assembly 500, the piston 511 is free to move between ring 521 and anvil 531.

The grasping elements 400a and 400b are shown in FIG. 8a-8d. The task of grasping elements 400a and 400b is to hold the probe unit 530 at a fixed position after activation of the device, and penetration of the probing needles 532a-532c to the tissue until reaching the sternum. More specifically, probing needles cannot penetrate the sternum, but alternatively, they are stopped by the sternum. Upon reaching this position, the grasping elements 400a and 400b hold and fix the anvil 531 at that position relative to the rest of device 1. The internal surfaces 402 of the grasping elements 400a and 400b respectively act essentially as rulers. More specifically, these internal surfaces are made rough, such that they can hold the anvil 531 at a fixed position relative to the device 1 at the appropriate time as described above. Furthermore, the beveled proximal faces 407 and 408 of extensions 403 and 404 respectively are beveled, such that upon pulling the trigger 200, said grasping elements 400a and 400b are forcibly pushed inside toward the internal space of barrel 100, to finally hold the anvil 531 of the probe unit 530. The elastic wings 405a and 405b, and 406a and 406b prevent the grasping elements from entirely falling to within the space of barrel 100.

Figure 9:
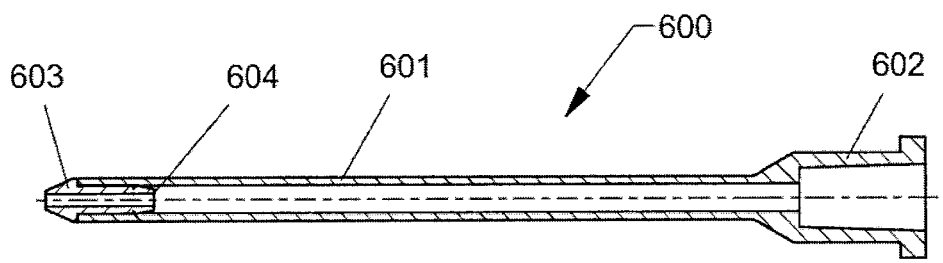
FIG. 9 is a cross sectional view of the cannula.

FIG. 9 shows the cross section of cannula 600. The cannula comprises an elastic tube 601 having hub 602, and a distal rigid spearhead 603. As note herein above, the face 604 of cannula 600 is forcibly pushed to a limited depth within the bone by the face 515 at the end of the stylet 513.

Figure 10A:
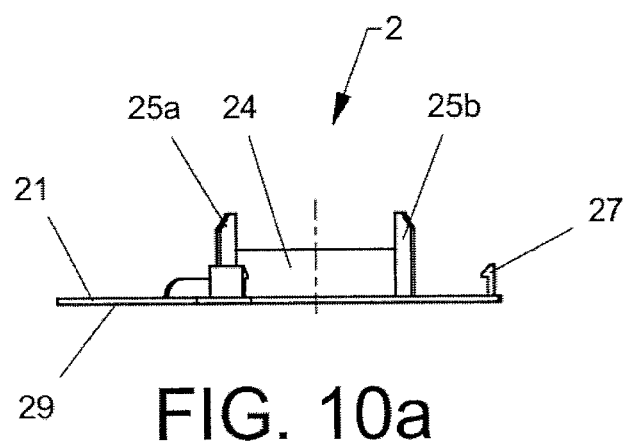
FIGS. 10a-10c show various views of the positioning element.
Figure 10B:
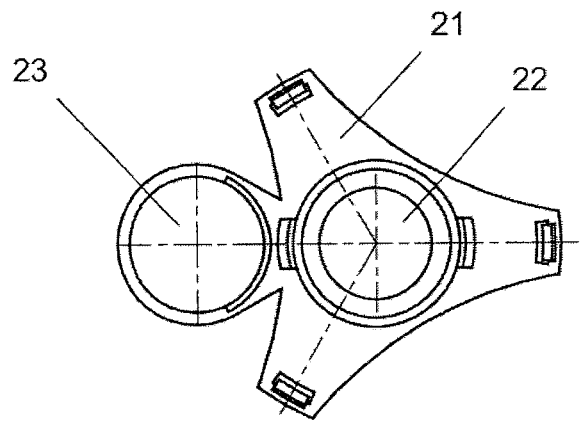
Figure 10C:
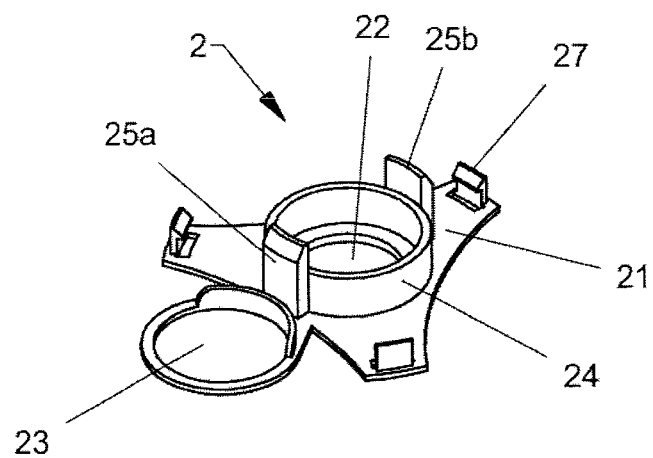

The structure of the positioning element 2 is shown in FIGS. 10a-10c. The positioning element is firstly used for determining the exact point of penetration into the sternum. The positioning element 2 also unlocks the second safety means of the device, therefore enabling activation of the device only when placed exactly and directly above the sternum. The positioning element comprises a base 21, a central round opening 22, and a side opening 23. A cylinder 24 is positioned axially to central opening 22. Cylinder 24 in turn comprises two opposing beveled fingers 25a and 25b. Said two fingers are used for unlocking the second safety means of the device 1, when the device 1 is appropriately placed on the positioning element 2. The positioning element also comprises at its periphery several snaps 27 for maintaining the cover 3, to protect the cannula 600 upon completion of the procedure, or when there is no need to use the portal of the cannula to within the bone. The bottom surface of the positioning element 2 comprises an adhesive layer 29, for fixing the positioning element of the patient's body.

Figure 11A:
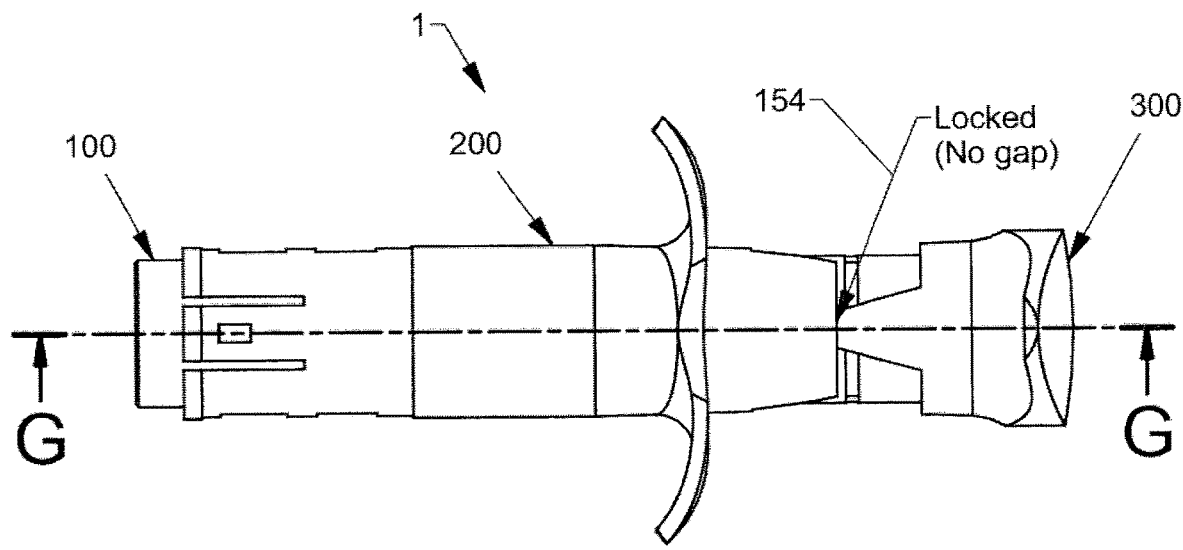
FIGS. 11a-11d show various views of the device of the invention.
Figure 11B:
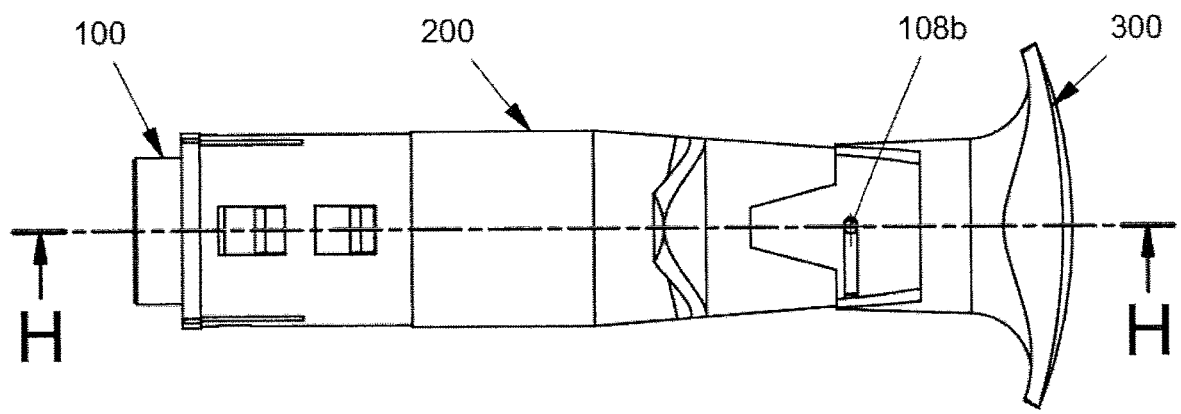
Figure 11C:
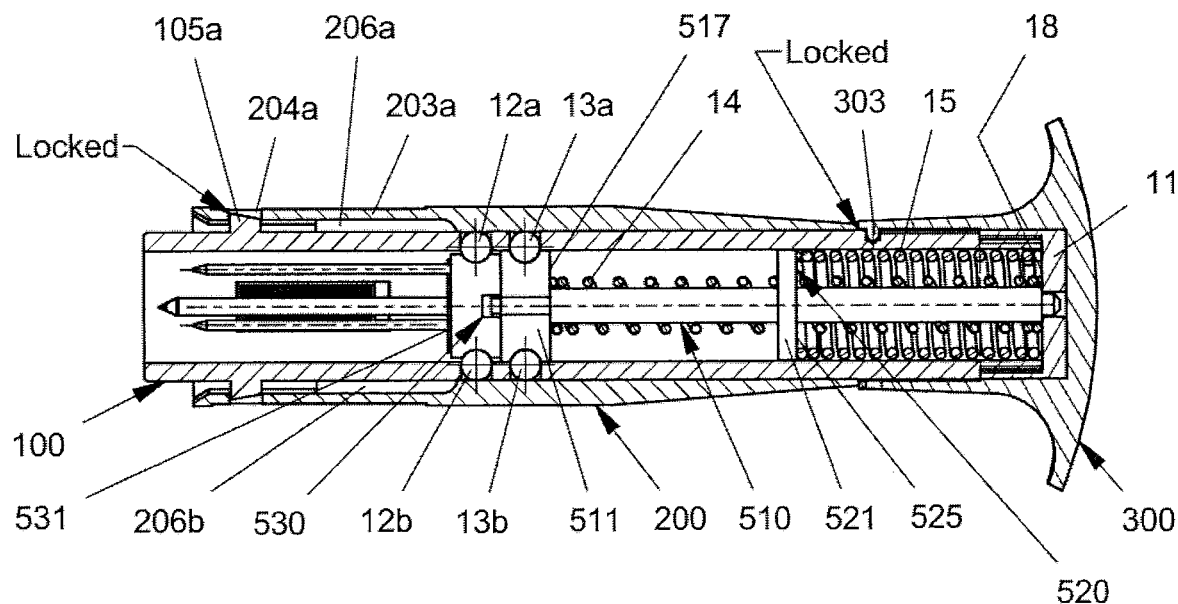
Figure 11D:
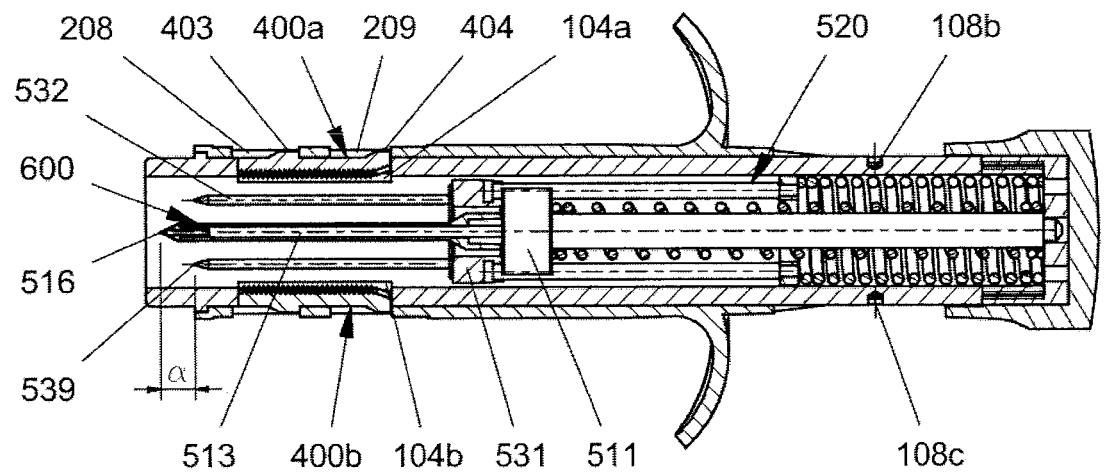

FIGS. 11a-11d show the device 1 in its cocked state. FIG. 11a shows a side view of device 1, FIG. 11b shows a top view of device 1, FIG. 11c shows a cross sectional view of device 1, made along plane G-G of FIG. 11a, and FIG. 11d shows a cross sectional view of device 1, made along plane H-H of FIG. 11b (for the sake of clarity, the decorative jacket 16 that appears in FIGS. 2 and 3, and in various other figures has been eliminated from these figures). Main spring 14 of the second driving means is positioned loaded between face 517 of piston 511, and face 18 of rear cap 11. Moreover, the main spring 14 is positioned within the internal space of secondary spring 15. Secondary spring 15 of the first driving means, in turn, is positioned loaded between face 525 of ring 521 and face 18 of rear cap 11. At this stage, the needle assembly is combined in a manner as shown in FIG. 7a. Main spring 14 is kept loaded by means of the balls 13a and 13b that lock and prevent any movement of the piston 511, and the secondary spring 15 is in turn kept loaded by means of balls 12a and 12b that lock and prevent any movement of the anvil 531. Moreover, windows 204a and 204b of snaps 203a and 203b respectively accommodate the protrusions 105a and 105b, therefore coupling together the trigger 200 and barrel 100. Furthermore, the safety catch 300 is positioned such that its indexing protrusion 303 is positioned at recess 108a. At this stage, there is no gap 154 between the trigger 200 and safety catch 300. This "no gap" state is shown in FIG. 11a. Furthermore, the grasping elements 400a and 400b are positioned within windows 104a and 104b of barrel 100 as show in FIG. 11d. At this stage the extensions 403 and 404 are positioned inside windows 208 and 209 of the trigger 200. As also shown in FIG. 11d, at this cocked state there is a constant difference of axial length .alpha. between the distal end 516 of stylet 513 and the distal ends 539 of the probing needles 532. The difference $\alpha$ is very important, as it defines the penetration depth (typically 6 mm beyond the sternum surface) into the sternum, as measured from the external surface of the sternum.

Figure 12C:
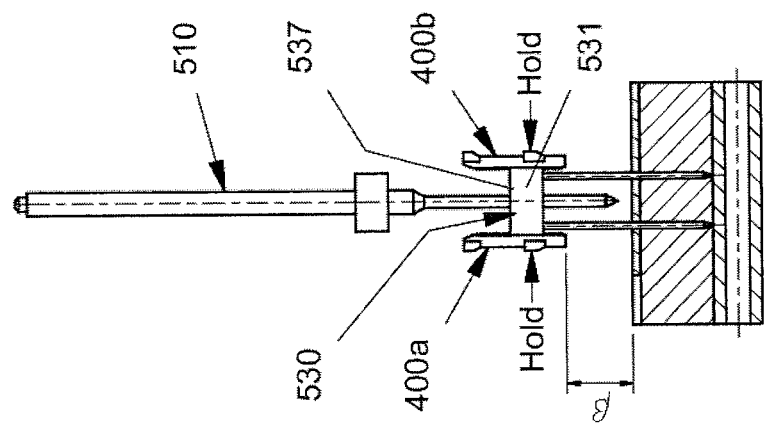
FIGS. 12a-12e illustrate the principle by which the penetration depth into the sternum is ensured by the device of the invention, irrespective of the tissue thickness.
Figure 12B:
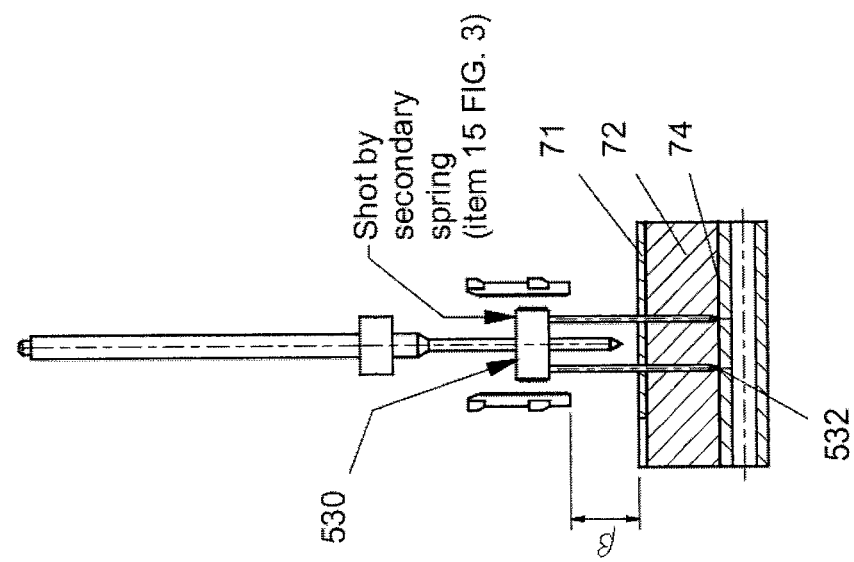
Figure 12A:
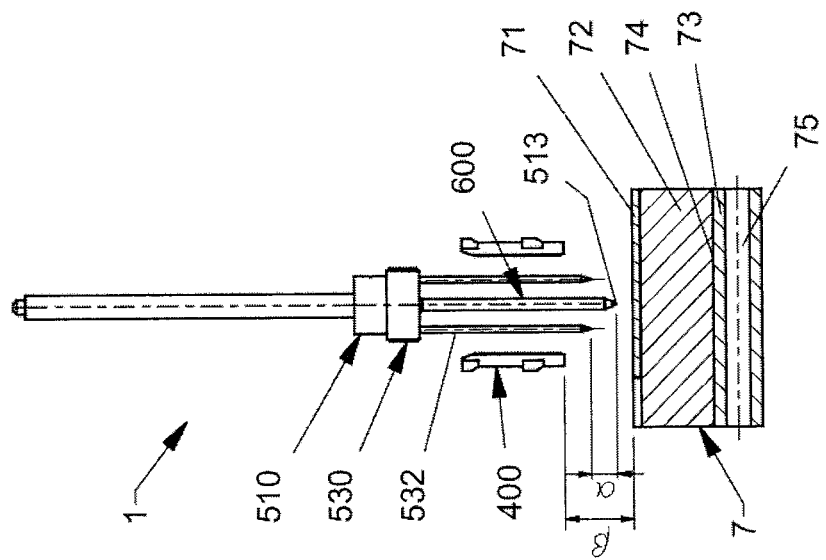
Figure 12E:
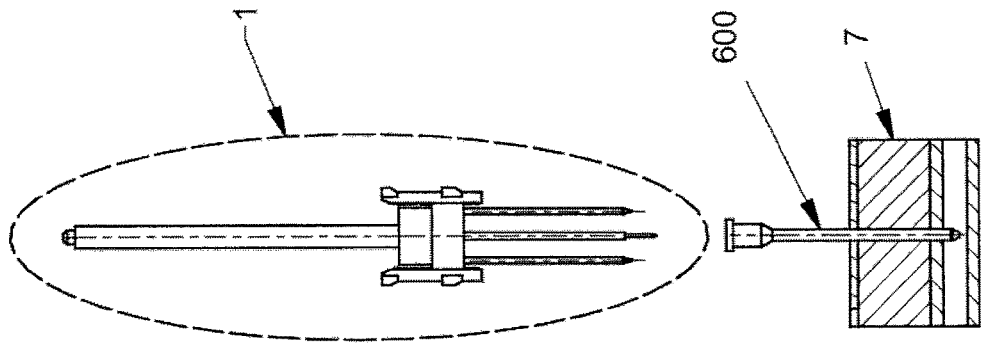
Figure 12D:
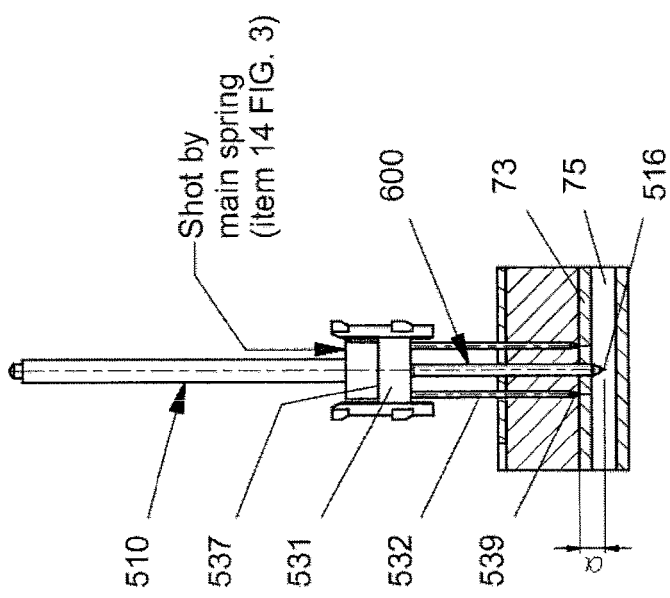

The principle by which the penetration depth into the sternum is ensured irrespective of the tissue thickness is described in FIGS. 12a-12e. FIG. 12a shows the "step a" of the procedure before activation. The body of the patient is indicated by numeral 7, and comprises skin 71, fat 72, sternum bone 73, wherein the bone surface is indicated by numeral 74, and the bone marrow is indicated by numeral 75. It is known in the art that the distance between the sternum surface 74 and sternum marrow 75 is essentially constant. However, the thickness of the tissue above the sternum, which comprises the skin 71 and fat 72 may very significantly vary between various people (for example, between 3 to 30 mm). As shown in FIG. 12a, the device is so designed that the distance .beta. between the grasping elements 400 and the patient's skin is constant. As previously noted, the object of the device of the invention is to penetrate the cannula into a predefined depth .alpha. within the sternum bone. FIGS. 12b-12d describe the series of steps that the device automatically performs for completing this task.

FIG. 12b shows the "step b" of the procedure, just after the device activation. At this stage, probing needles 532 of the probe unit 530 penetrate the patient's tissue, until they reach the sternum bone, and stop by rigidity of the bone surface 74.

FIG. 12c shows the "step c" of the procedure. Grasping elements 400a and 400b hold the probe unit 530, preventing any axial movement of the probe. In this situation, the proximal surface 537 of anvil 531 defines an axial movement limit for the hammer 510.

FIG. 12d shows the "step d" of the procedure. The hammer is axially pushed towards the sternum bone, until reaching its movement limit as defined in "step b" by the proximal surface 537 of anvil 531. As the previously stated, the stylet penetration depth α is obtained, as this is the difference in axial length between the distal end 516 of stylet 513 and the distal ends 539 of the probing needles 532.

FIG. 12e shows the final "step e" of the procedure. In this step, the device 1 is pulled to the proximal direction, leaving only the cannula 600 fixed within the sternum.

The operation of the device 1 by which the penetration depth into the sternum is ensured irrespective of the tissue thickness is described in FIGS. 13a-13h. In "state 1" shown in FIGS. 13a and 13b, the positioning element 2 is mounted on the patient's chest. The user puts his finger into side opening 23, moving the positioning element until he finds the sternal notch 8 (see FIG. 1). Next, the user adjusts the positioning element 2 such that it is just down from the sternal notch. When adjusted, the central round opening 22 defines the site of penetration, and the user sticks the positioning element at this location.

In "state 2" shown in FIG. 13c the user brings the device close to the positioning element 2. At this state, the device is still locked by two safety means, i.e., by the safety catch 300 (first safety means) still in its "locked state", and by the second safety means still in its "locked state" as long as the device is not appropriately positioned at its defined position on the positioning element 2. As long as the first safety means is locked, there is no gap 154 between safety catch 300 and trigger 200, as shown in the figure.

In "state 3" shown in FIG. 13d the user releases the first safety means, by rotating (for example, 90° rotation) the safety catch 300. At this state, the device is still locked by the second safety means, as the device is not yet appropriately positioned over the positioning element 2.

In "state 4" shown in FIG. 13e the user positions the device over the positioning element 2. The positioning location is limited such that the device can be positioned only in the appropriate manner. More specifically, the appropriate position is defined such that the snaps 203a and 203b of the device are located against fingers 25a and 25b of the positioning element 2. The device cannot be positioned over the positioning element 2 unless mounted in said appropriate position. When appropriately positioned, fingers 25a and 25b open the snaps 203a and 203b, thereby releasing the trigger 200 from its previously coupled state to the barrel 100. In other words, this appropriate positioning of the device 1 on the positioning element release said second safety means. It should be noted that if the user decides not to activate the device, he can still pull the device from the positioning element, and the second safety means is automatically locked again. If the user so decides, he may also manually lock the first safety means by rotating the safety catch 300. Such double safety means significantly increase the safety and reliability of the device operation.

In "state 5" shown in FIG. 13f the user squeezes the device trigger until there is no gap 155 between trigger 200 and safety catch 300. This operation activates the device, resulting in the performance of "step b", "step c" and "step d", as shown and described with respect to FIGS. 12b-12d.

In "state 6" shown in FIG. 13g the user pulls the device 1 from the positioning element 2, leaving only the cannula 600 fixed within the bone. In such a manner, the user may use the channel of the cannula in order to inject drugs to within the sternum marrow.

In "state 7" shown in FIG. 13h the user covers the cannula by putting cover 3 over the positioning element. The peripheral snaps 27 of the positioning element 2 lock the cover on its place.

Figure 14A:
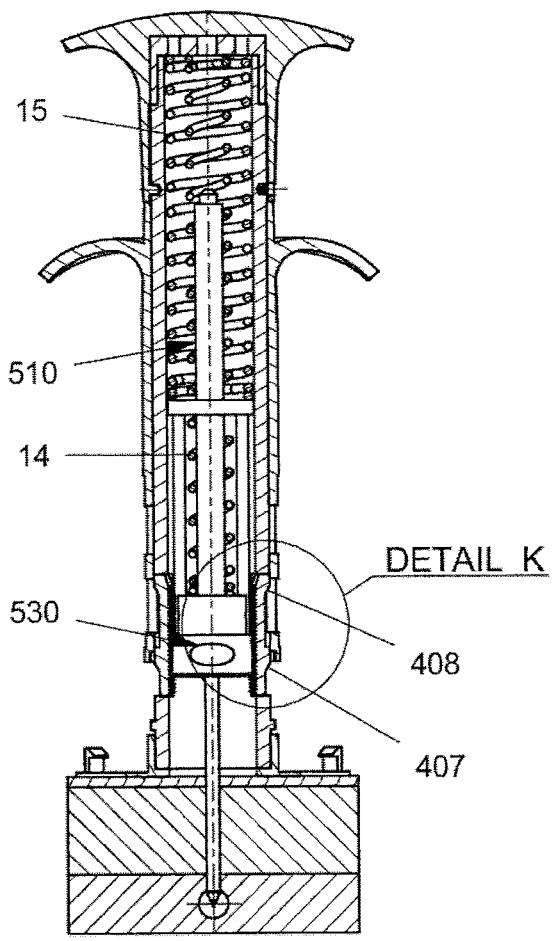
FIGS. 14a-14c show in more detail some of the various steps of FIGS. 13a-13h.
Figure 14B:
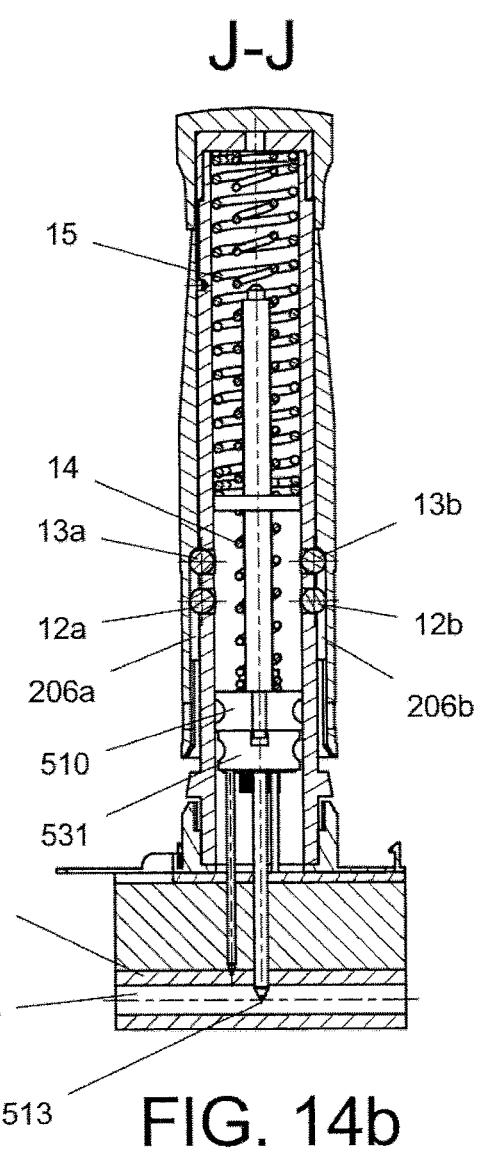
Figure 14C:
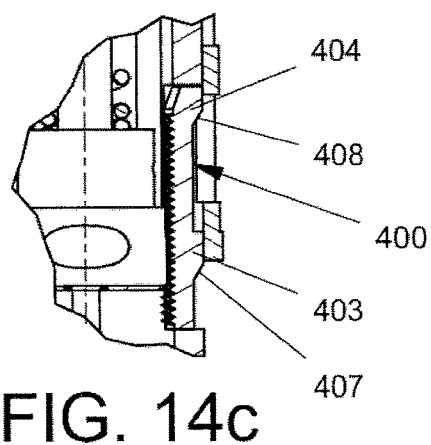

FIGS. 11c and 14a-14c describe in more detail the activation of the device, as in state 5 above. After positioning the device on the positioning element 2, and unlocking the two safety means, the user carefully squeezes the trigger 200. Initially, balls 12a and 12b that previously locked the probe needles at the anvil 531 (this state is shown in FIG. 11c), come to within grooves 206a and 206b, thereby releasing the anvil 531. The released secondary spring 15 of the first driving means transfers a force and pushes the probe unit 530 toward the bone. After reaching the sternum bone, the user continues to squeeze the trigger, thereby the trigger applies a radial force on the beveled faces 407 and 408, causing the grasping elements to enter into the barrel 100 as shown in FIG. 14c, thereby holding the anvil in a fixed position. Next, as the user continues to squeeze the trigger, balls 13a and 13b come to within the grooves 206a and 206b respectively, thereby releasing the previously locked hammer 510 of the second driving means. The unlocking of the hammer 510 transfers a force and causes the hammer to move forward until reaching the anvil, and stopping at this position. The hammer movement causes the stylet 513 to penetrate the sternum bone to a depth of α.

As described above, the present invention provides an automatic intraosseous device that can introduce a cannula to a specific depth of a bone, irrespective of the thickness of the tissue above the bone. The invention also provides a kit which comprises, in additional to the intraosseous device, means for accurately determining the right location for penetration, particularly when this location is the sternum. The invention as described also provides second safety means at the device that prevents operation of the device, and unlocking means at the positioning element, that release the device from its locked position only when the device is positioned at the right location for penetration (i.e., at the positioning element), while preventing any operation at other locations. Said second safety means are provided in additional to the first safety means that have the form of a safety catch. The present invention also provides all said features and advantages in a device which is fully automatic. All the above are only some of the features and advantages of the device of the present invention.

While some embodiments of the invention have been described by way of illustration, it will be apparent that the invention can be carried out with many modifications, variations and adaptations, and with the use of numerous equivalents or alternative solutions that are within the scope of persons skilled in the art, without departing from the spirit of the invention or exceeding the scope of the claims.

The invention claimed is:

1. An intraosseous device, comprising:
   a) a cannula through which life-saving fluids are transfusible into or out of bone marrow of a target bone when said cannula is penetrated into the target bone;
   b) a stylet which is engageable with said cannula; and
   c) means for automatically adjusting a depth of insertion of said stylet within the target bone to a thickness of tissue above the target bone, said automatic adjusting means comprising first driving means operable to drive a pointed object associated with said stylet to a point of contact with a surface of the target bone, and second driving means responsive to a triggered action,
   wherein said first driving means comprises a force absorbing unit and a first force transmitting unit configured to transmit an applied force to said pointed object that drives said pointed object to the point of contact with a surface of the target bone, and said second driving means comprises a second force transmitting unit and a movable stylet-driving member, wherein a first reference element of said first driving means and a second reference element of said second driving means are retained in a retracted position together with said stylet and cannula, such that, at the retracted position, said first reference element is spaced from said second reference element by a distance $\alpha$,
   wherein said second force transmitting unit is configured to transmit a force initiated by the triggered action to said stylet-driving member which causes said stylet together with said cannula, when mutually engaged, to be driven within the target bone until movement of said stylet-driving member is limited by said force absorbing unit, said first reference element is spaced from said second reference element by said distance a at a driven position, and a distal tip of said stylet is penetrated within the target bone by a predefined depth within the target bone with respect to an outer surface of the target bone equal to said distance $\alpha$, said depth being irrespective of the thickness of tissue above the target bone.

2. The device according to claim 1, further comprising a trigger for activating the second driving means.

3. The device according to claim 2, wherein the trigger is also configured to activate the first driving means.

4. The device according to claim 3, wherein the trigger, when actuated, is operable to cause automatic operation of the second driving means subsequent to operation of the first driving means.

5. The device according to claim 1, wherein the cannula is configured with a proximal hub for flow therethrough of the life-saving fluids, a rigid distal end, and an elastic tube extending between said hub and said cannula distal end.

6. The device according to claim 1, further comprising a hollow device body within which at least the stylet, cannula, and first and second force transmitting units are retained in the retracted position.

7. The device according to claim 6, wherein the first driving means further comprises a probing needle constituting the pointed object which is retained in the retracted position within the device body together with said stylet and cannula, and a distal tip of said probing needle is the first reference element.

8. The device according to claim 7, wherein the force absorbing unit is a movement limiting surface positioned proximally to the distal tip of said probing needle.

9. The device according to claim 1, wherein each of the first and second force transmitting units comprises at least a resilient element.

10. The device according to claim 1, wherein the first reference element is spaced proximally from the second reference element by the distance $\alpha$ when the first and second reference elements are set at the retracted position.

11. A method for inserting a cannula within a bone, comprising the steps of:
    a) providing first and second reference elements that are independently displaceable from a retracted position to a driven position, wherein said second reference element is fixedly spaced from a cannula by a second distance and, at the retracted position, is spaced from said first reference element by a distance $\alpha$;
    b) distally driving a pointed object through body tissue, by a force transmitting unit configured to transmit an applied force to said pointed object that drives said pointed object to a point of contact with an outer surface of a target bone, until said pointed object contacts the outer surface of the target bone, wherein said first reference element is fixedly spaced from said pointed object by a first distance;
    c) actuating a trigger; and
    d) distally driving said cannula with use of a plurality of cooperating mechanical elements configured such that at least a first of the cooperating mechanical elements cooperates with the actuated trigger and a second of the cooperating mechanical elements cooperates with a force absorbing unit connected to said distally driven pointed object, until movement of said second of the cooperating mechanical elements is limited by said force absorbing unit, said first reference element is spaced from said second reference element by said distance $\alpha$ at the driven position, and said cannula is penetrated within the target bone to a predefined depth with respect to the outer surface of the target bone which is irrespective of a thickness of the tissue above the target bone.

12. The method according to claim 11, wherein the second reference element is spaced from the first reference element by a distance greater than the distance a after the pointed object has been driven through the body tissue until contacting the outer surface of the target bone and before the cannula has been distally driven.

13. The method according to claim 11, further comprising the step of transfusing life-saving fluids through the cannula into or out of a bone marrow cavity of the target bone when the cannula is penetrated into the target bone.

* * * * *